United States Patent
Ahring et al.

(10) Patent No.: US 8,506,716 B2
(45) Date of Patent: Aug. 13, 2013

(54) METHOD FOR TREATING BIOMASS AND ORGANIC WASTE WITH THE PURPOSE OF GENERATING DESIRED BIOLOGICALLY BASED PRODUCTS

(75) Inventors: Birgitte Kiær Ahring, Hørsholm (DK); Jens Munck, Allerød (DK)

(73) Assignee: Cambi Bioethanol APS, Copenhagen NV (DK)

( * ) Notice: Subject to any disclaimer, the term of this patent is extended or adjusted under 35 U.S.C. 154(b) by 1158 days.

(21) Appl. No.: 11/575,868

(22) PCT Filed: Sep. 23, 2005

(86) PCT No.: PCT/DK2005/000603
§ 371 (c)(1),
(2), (4) Date: Nov. 23, 2007

(87) PCT Pub. No.: WO2006/032282
PCT Pub. Date: Mar. 30, 2006

(65) Prior Publication Data
US 2009/0178671 A1    Jul. 16, 2009

(30) Foreign Application Priority Data
Sep. 24, 2004 (DK) ................................. 2004 01459

(51) Int. Cl.
*C13K 1/02* (2006.01)
(52) U.S. Cl.
CPC ............ *C13K 1/02* (2013.01); *C12P 2201/00* (2013.01)
USPC ......................................................... 127/37
(58) Field of Classification Search
USPC ............... 127/36, 37, 42, 43, 44, 45; 162/21, 162/65, 78
See application file for complete search history.

(56) References Cited

U.S. PATENT DOCUMENTS

| | | | |
|---|---|---|---|
| 2,690,425 A | 9/1954 | Moses et al. | |
| 4,461,648 A | 7/1984 | Foody | |
| 5,171,592 A | 12/1992 | Holtzapple et al. | |
| 5,865,898 A | 2/1999 | Holtzapple et al. | |
| 6,419,788 B1 * | 7/2002 | Wingerson | 162/14 |
| 6,555,350 B2 * | 4/2003 | Ahring et al. | 435/162 |

FOREIGN PATENT DOCUMENTS

| | | |
|---|---|---|
| JP | 2002126794 | 5/2002 |
| JP | 2003039045 | 2/2003 |
| WO | WO 00/01420 A1 | 1/2000 |

OTHER PUBLICATIONS

Klinke et al., Characterization of degradation products from alkaline wet oxidation of wheat straw, Bioresource Technology 82 (2002) 15-26, Elsevier Science Ltd.
Van Walsum et al., Conversion of Lignocellulosics Pretreated with Liquid Hot Water to Ethanol, Applied Biochemistry and Biotechnology vol. 57/58, 1996, Humana Press Inc.

* cited by examiner

*Primary Examiner* — David M Brunsman
(74) *Attorney, Agent, or Firm* — B. Aaron Schulman, Esq.; Stites & Harbison, PLLC.

(57) ABSTRACT

The present invention provides a method for treatment of lignocellulosic organic waste or biomass, by which the carbohydrates are rendered more available for subsequent hydrolysis, e.g. by means of addition of enzymes or direct fermentation to one or more desired products. The invention more specifically relates to a method comprising a combination of the following process steps: thermal hydrolysis, wet oxidation and wet explosion. The method according to the present invention can operate with undivided or only poorly divided substrate having a high dry matter concentration.

13 Claims, 5 Drawing Sheets

METHOD FOR TREATING BIOMASS AND ORGANIC WASTE WITH THE PURPOSE OF GENERATING DESIRED BIOLOGICALLY BASED PRODUCTS

This application is a 371 of PCT/DK05/00603 filed Sep. 23, 2005.

INTRODUCTION

Within the last few decades focus on renewable resources has increased considerably. The complex chemical structure of biomass and other organic materials, primarily the bonds between lignin, cellulose and hemicellulose, limits the possibility of utilizing the sugars present in cellulose and hemicellulose respectively.

All types of materials made up of lignocellulosic biomass or organic waste that contains considerable amounts of lignin, but preferably such with more than 5% (w/w) as for example straw, wood, fibres, baits, paper pulp, slurry and household waste, can advantageously be treated by a method according to the present invention, at which the carbohydrate fractions (e.g. cellulose and hemicellulose) become available for further hydrolysis and fermentation.

FIELD OF THE INVENTION

The invention relates to the technical field that comprises treatment of lignocellulosic organic waste or biomass, by which the treated substrate's content of sugars and the like is rendered more available for hydrolysis, e.g. by means of addition of enzymes or direct fermentation to one or more desired products. The invention more specifically relates to a method comprising a combination of the following process steps: 1) thermal hydrolysis 2) wet oxidation and 3) wet explosion ("flashing" by momentary reduction of pressure). The total energy consumption of this combination of processes is low.

DESCRIPTION OF THE INVENTION

Pre-Treatment Prior to the Wet Oxidation Process

The material to be treated is, if necessary, divided to particle sizes below 50 cm, but preferably to sizes between 0.5 and 25 cm. Pre-treatment and heating of the material is carried out under addition of recirculated process water, recirculated steam and fresh steam. Depending on the composition of the material and the desired end-product the pH-value and the salt balance may be adjusted with acid/base and/or other chemicals. Furthermore, in order to increase the final yield of ethanol, the lignocellulosic material may optionally be subjected to an acidic treatment as is further described in e.g. example 4 below. The duration of the pre-treatment is typically between 0.1-48 hours at room temperature. However, the pre-treatment time may be reduced by increasing the temperature. In such case the preferred temperature is 50-110° C.

The dry matter content of the lignocellulosic material can be 10-50% depending on the content of salt in the material, but is preferably in the interval 15-50%, more preferably in the interval 20-50%, such as 25-50%, even more preferably in the interval 30-50%, such as 35-50% and most preferable in the interval 40-50%, such as 45-50%.

Thermal Hydrolysis

The optionally pre-treated material is transferred to a reactor, where the lignocellulosic material is mixed and heated with direct or indirect steam to 140-200° C., preferably 150-190° C., more preferably 160-180° C. and most preferably 170° C., at saturation pressure. When the desired temperature and the desired pressure have been reached, the material is maintained under these conditions for 5-30 min, preferably 10-25 min, more preferably 10-20 min and most preferably 15-20 min.

Wet Oxidation

After termination of the thermal hydrolysis an appropriate oxidizing agent is added to the lignocellulosic material, preferably oxygen, hydrogen peroxide or air, in an amount that depends on the content of lignin and that typically corresponds to 2-20% of the COD (chemical oxygen demand) content of the material, preferably 3-19%, more preferably 5-17%, such as preferably 7-16%, more preferably 8-15%, such as preferably 9-14%, more preferably 10-13% and determined by the pressure development in the reactor.

Pressure and temperature are increased in connection with the wet oxidation to 15-35 bar, preferably 20-35 bar, more preferably 25-35 bar and most preferably 30-35 bar and 170-210° C., preferably 180-200° C., more preferably 190-200° C. respectively. When the desired pressure and the desired temperature have been reached after the addition of the oxidizing agent, this condition is maintained for 1-30 min, preferably 5-25 min, more preferably 10-20 min and most preferably 15-20 min. Optionally, after termination of the wet oxidation reaction the pressure of the lignocellulosic material may be released to 5-10 bar rendering the claimed interval of pressure at which the momentary decompression (i.e. the wet explosion) can be performed, 5-35 bar.

Wet Explosion

The oxidized material is hereafter led to a flash tank, at which the pressure is reduced from 5-35 bar, preferably 15-35 bar to approximately 1 bar, i.e. atmospheric pressure. During this wet explosion most cell structures are disintegrated. Waste steam from the wet explosion is entrapped and utilized in the above mentioned pre-treatment of the material. Immediately after the wet explosion the temperature of the oxidized material is preferably 95-110° C. rendering the material sterile.

Further Processing

After cooling to the desired temperature depending on the end product, the treated material can be further processed to ethanol, hydrogen, lactic acid, methane, succinate, organic acids or other desired products.

BACKGROUND ART

Different kinds of treatment of material by which the treated substrate's content of sugars and the like are made more available have been described in literature. The most well-known are: a) Strong and weak acid hydrolysis, b) wet explosion (Steam Explosion—STEX), c) wet oxidation (WO), d) basic fibre explosion (Ammonia Fibre Explosion—AFEX), e) thermal hydrolysis (Liquid Hot Water—LHW) and e) thermal hydrolysis with addition of base and oxidizing agent.

Strong and Weak Acid Hydrolysis

The described types of strong and weak acid hydrolysis are characterized in that hemicellulose is hydrolyzed and thereby dissolved concurrently with the availability of cellulose being increased for a subsequent acid-based or enzymatic hydrolysis. When using these methods it is, after separation of the insoluble and the dissolved fractions, possible to process these fractions further among others by means of fermentation.

The strong acid hydrolysis has among others been described by Lightner (U.S. Pat. No. 6,258,175), where also the possibility of re-using the applied acid after precipitation with ethanol is described. The primary purpose of the process is to dissolve cellulose and hemicellulose for subsequent use in e.g. production of ethanol by means of fermentation. U.S. Pat. Nos. 6,022,419, 5,705,369, 5,503,996, 5,424,417, 5,125, 977 and FR 2.580.669 describe the weak acid hydrolysis (single- and multi-step process) that is used in the separation of cellulose and hemicellulose from the other components in the biomass. Hemicellulose is dissolved in the acid hydrolysis, and a smaller fraction of the lignin is furthermore dissolved. The described processes moreover comprise separation of hemicellulose (in dissolved form) and cellulose (as solid fraction).

There are several problems connected with acid hydrolysis of biomass. Firstly it is necessary to divide the material to very fine particles (<1 mm), which is extremely energy demanding. Furthermore, a neutralization of the treated material is required, which is normally carried out by addition of $CaCO_3$ (limestone). This means that the consumption of chemicals in the process is high concurrently with a considerable amount of hydrated calcium sulphate being accumulated by the neutralization process. Moreover, the treated material from the acid hydrolysis has an inhibiting effect on enzyme hydrolysis and microbial fermentation compared to material resulting form other forms of treatment (see below). Finally, pumps, reactors and the like are exposed to corrosion as a result of the acid-catalyzed process.

Wet Explosion

Wet explosion (STEX) was described as far back as 1928, where Mason developed the process for manufacturing hardboards (U.S. Pat. No. 1,824,221 and U.S. Pat. No. 2,759,856). The STEX process consists of thermal hydrolysis under high pressure, whereafter the pressure is released in a so-called "flash effect", where an explosion of each fibre takes place due to the great drop of pressure—hence the name wet explosion (or steam explosion). This method of treatment has later on been further developed for the manufacture of e.g. ethanol (Morjanoff and Gray 1987) and paper (WO 98/27.269). GB patent application 2.145.090 relates to a three-step hydrolysis process for the treatment of lignocellulosic organic material by means of high temperatures and pressure, by which pentose-, hexose- and lignin-fractions are separated in three separate steps. Moreover, the process comprises cooling by "flash evaporation" with the aim of preventing the resulting sugars from dissociating. However, these process steps require a high degree of mechanical division and do not comprise the addition of oxidizing agents, the use of which have shown to be advantageous in connection with methods according to the present invention.

In STEX normally a partial dissolution of hemicellulose (>80%) takes place, and cellulose is made available for subsequent hydrolysis. The effect of STEX resembles the effect of acid hydrolysis—however, the STEX process exposes the process equipment to far lesser wear and is not so demanding as regards the use of chemicals and accumulation of waste. However, in STEX there is still a considerable formation of substances that inhibit a possible subsequent fermentation process (Palmqvist and Hahn-Hägerdal 2000) particularly when the material previously has been liquified with acid ($SO_2$ or $H_2SO_4$ (Martin et al. 2002)). Furthermore, no noticeable decomposition of lignin takes place in STEX, wherefore the lignin is still able to effect a possible enzymatic hydrolysis.

Wet Oxidation

Wet oxidation (WO) has been developed in order to oxidize organic waste fractions (U.S. Pat. No. 2,690,425) and has later on been modified so as to obtain a solution of hemicellulose from lignocellulose-containing biomass and organic waste (WO 0014120). Wet oxidation comprises a thermal process with addition of an excess of pressure of oxygen as well as a basic catalyst, whereby the hemicellulose is partially dissolved and a part of the present lignin oxidized. Hereby the availability of cellulose is increased. Compared with STEX and acid hydrolysis, in WO only a partial dissolution of hemicellulose takes place (Bjerre et al. 1996). Normally, WO does not require an extra process step for the removal of inhibiting substances. Klinke et al. (2002) describes that the concentration of these inhibiting substances is considerably smaller in a wet oxidation process compared with STEX and acid hydrolysis. WO 0014120 describes a method for dissolution of hemicellulose in lignocellulose-containing materials (primarily leguminous plant sources). The method comprises heating of biomass in an aqueous medium in the presence of an oxidizing agent, in this case oxygen. However, this method does not, as the methods according to the present invention, comprise a "flashing process". The wet oxidation process has previously shown to be effective at biomass concentrations over 100 g of dry matter/l or on material having particle sizes above 10 mm. Both of these limitations are damaging for the process economy when producing af large-scale. Neither do the described processes permit a re-use of steam, which again has a negative influence on the process economy.

Basic Fibre Explosion

Basic fibre explosion (AFEX) is a process that combines steam explosion and addition of a basic catalyst for treatment of different types of biomass for improving feedstuff or for a further fermentation to e.g. ethanol (U.S. Pat. No. 5,171,592). U.S. Pat. No. 5,865,898 describes a process for treatment of lignocellulose-containing biomasses, which comprises addition of calcium oxide or calcium hydroxide and an oxidizing agent followed by heating to a relatively high temperature (however always below 100° C. in order not to decompose the lignocellulose-containing biomass). In traditional AFEX the biomass is liquified in ammonia water at moderate temperatures (~50° C.), after which the pressure is momentary released (explosion). By this process cellulose and lignin are modified, which makes the cellulose more reactive (available), concurrently with release of the hemicellulose. The process creates considerably fewer inhibiting substances than the acid-catalyzed processes, but typically there is a need for a further division of the material to a particle size of approximately 1.5 cm, which requires additional supply of energy (Holtzapple et al. 1991). Furthermore, only a modification of lignin takes place, which may be a problem in connection with a possible subsequent enzymatic hydrolysis and fermentation.

Thermal Hydrolysis

Thermal hydrolysis (LHW) is a process (170° C.-230° C.) in which a high dissolution of hemicellulose takes place concurrently with a partial dissolution of lignin and an improved availability of cellulose (for enzymatic hydrolysis). Waste of sugar cane that has not previously been divided and that has been pre-treated with LHW, results in up to 90% of the theoretic ethanol yield after enzymatic hydrolysis and fermentation after addition of moderate amounts of enzyme (Van Walsum et al. 1996). U.S. Pat. No. 4,461,648 describes a method that increases the availability of cellulose- and lignocellulose-containing materials. The method comprises the addition of water steam under pressure, heat treatment and wet explosion. The addition of an oxidizing agent is not described in connection with the described process. A disadvantage of the method is the lack of efficiency when processing higher concentrations of biomass.

LHW has solely been tested with biomass concentrations up to 100 g/l, and it is uncertain, how effective the process is at higher concentrations, which is a necessity for obtaining a economically profitable process—e.g. for the manufacture of ethanol.

Thermal Hydrolysis with Addition of Base and Oxidizer

Finally, U.S. Pat. No. 6,419,788 describes a method of treatment for purification of cellulose from biomass for the manufacture of paper, plastic, ethanol and other chemicals. The process consists of a combination of thermal hydrolysis and wet oxidation, where divided biomass (<1") is treated under steam pressure (180° C.-240° C.) under addition of an oxidizing agent as well as an alkaline catalyst in a countercurrent reactor. In the treatment a partial dissolution of hemicellulose as well as oxidation of lignin take place, whereby cellulose is purified in the solid fraction. However, this requires washing of the solid fraction under heat and pressure in order to wash-out residue lignin and hemicellulose. The process furthermore includes energy recovery, which contributes to optimize the process economy. However, the combined thermal hydrolysis and wet oxidation do require an energy-costly division of the biomass, and how large a part of the lignin that is actually removed by this process is furthermore unknown.

ADVANTAGES OF THE PRESENT INVENTION COMPARED TO PRIOR ART

The present method that combines thermal hydrolysis, wet oxidation and wet explosion, has several advantages compared to the methods described in the prior art.

The method can operate with dry matter concentrations of up to 50% without a reduction in effectiveness and offers an effective opening of lignocellulosic biomasses and waste. This means that the subsequent processing becomes more economical profitable compared to previously described wet oxidation processes.

Through the implementation of a wet explosion step as a part of the method according to the present invention an effective opening of all cell structures in the material is obtained. This means that the material is easily pumped and directly available for enzymatic hydrolysis.

By using methods according to the present invention it is possible to obtain a high yield of both hexoses and pentoses by addition of even small amounts of enzyme compared to other methods of treatment.

By using e.g. hydrogenperoxide as an oxidizing agent in the method according to the present invention a large part of the lignin is oxidized to organic compounds, which by fermentation may be further converted into ethanol, methane, hydrogen, organic acids or other products.

At the same time only small concentrations of inhibiting compounds are created by methods according to the present invention compared to other methods of treatment, such as acid hydrolysis or steam explosion. Therefore, the process water after the fermentation/processing can to a large extent be re-used.

Methods according to the present invention utilize the waste steam from the wet explosion, which reduces the need for external energy, i.e. electricity, natural gas or oil. Internal, useful energy will furthermore be created in connection with the wet oxidation.

At the same time the material is sterile after the treatment indicating that a method according to the present invention is particularly suitable for destruction of pathogens. The treated material may therefore optionally be stored under sterile conditions for longer periods. If the method is used in combination with base addition the process will lead to a destruction of prions, possibly existing in the material.

Also, the problems with heat exchange and cleansing of heat exchangers, which can be expensive when using other methods, is avoided using the method according to the present invention.

The combination of wet oxidation and wet explosion as well as direct steam injection according to the present invention makes it possible that material, that is not or only poorly divided, meaning that the material preferably are having particle/fiber sizes of more than 1.5 cm, preferably between 5-20 cm, can be processed. Methods according to the present invention may thus be used on material having particle sizes above 1.5 cm, preferably larger than 2 cm, such as larger than 3 cm, i.e. preferably larger than 4 cm, such as larger than 5 cm, i.e. preferably larger than 10 cm, such as larger than 15 cm, i.e. preferably larger than 20 cm, such as larger than 25 cm, i.e. preferably larger than 30 cm, such as larger than 35 cm, i.e. preferably larger than 40 cm, such as larger than 45 cm, i.e. up to 50 cm.

Methods according to the present invention are carried out as batch processes, which permit the process parameters, such as pressure, temperature, treatment time and concentration of oxidizing agents to be varied independently. This has a favorable effect on the possibility of controlling the development of inhibiting substances, the burning of sugars etc.

The residues from the methods according to the present invention, which will normally consist of low-molecular organic acids from the wet oxidation (as well as organic residues from the fermentation), may favorably be utilized in the manufacture of methane.

Recovery of waste steam from the wet explosion and the production of methane result in that the total process has a minimal external energy consumption and in certain cases produces an energy surplus.

EXAMPLE 1

Figure 1:
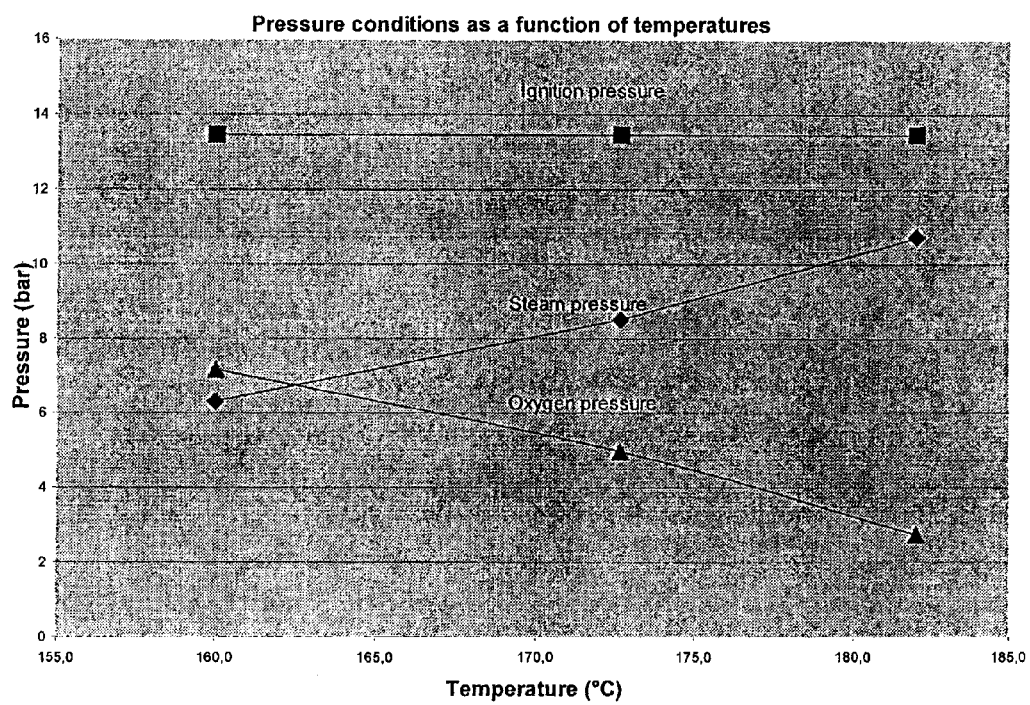
FIG. 1 is a graph showing the relationship between pressure and temperature in the treatment of straw.
Figure 2:
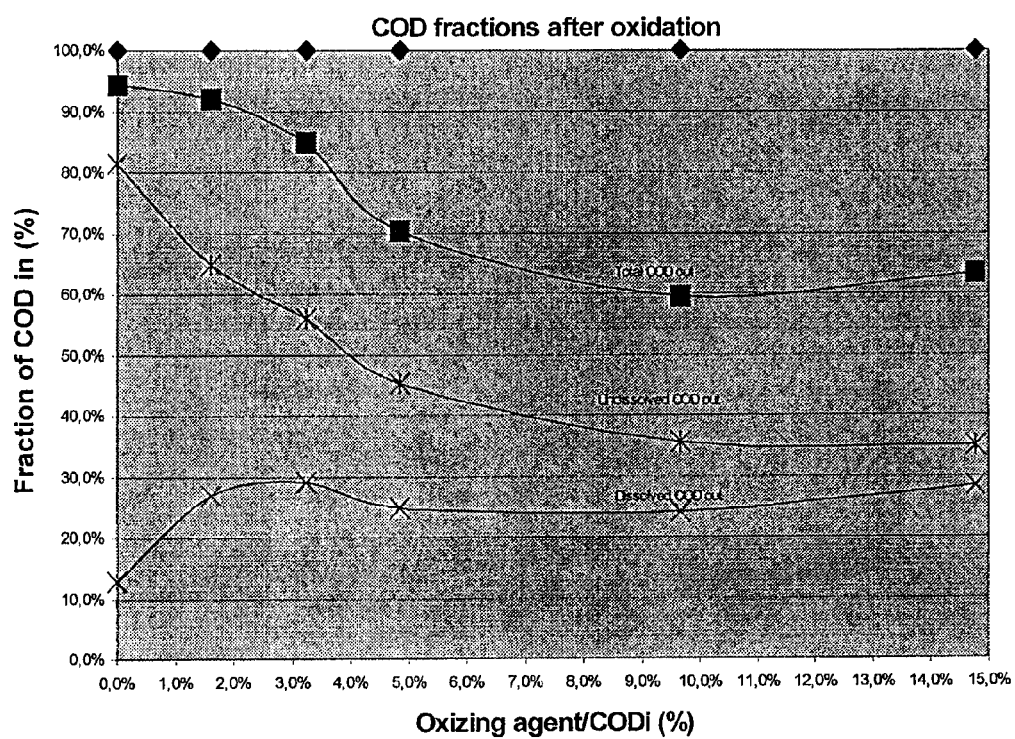
FIG. 2 is a graph showing the COD fraction resulting from the oxidation of straw.
Figure 3:
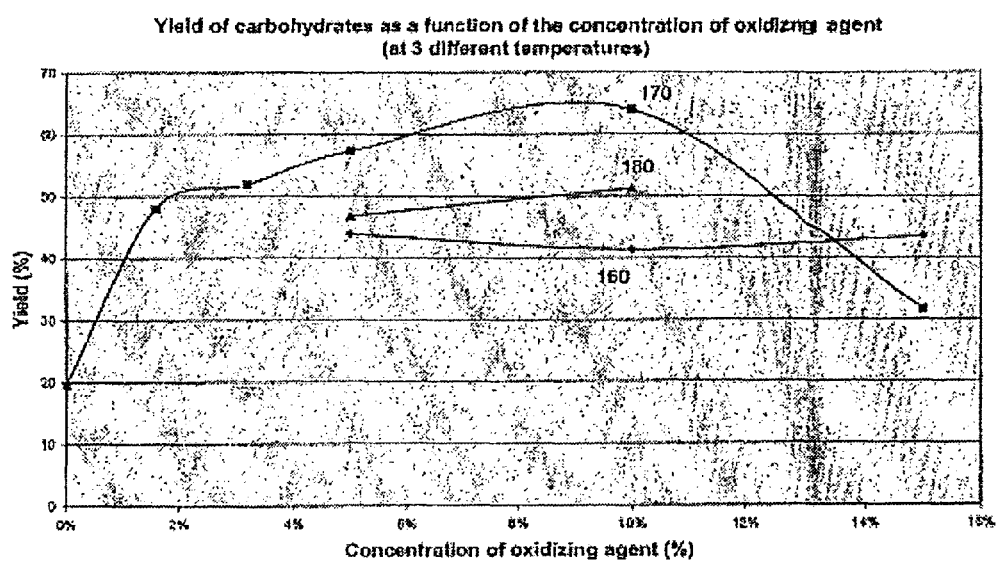
FIG. 3 is a graph showing the total yield of carbohydrates (%) resulting from the claimed treatment of straw as a function of different temperatures and different concentrations of oxidizing agent (hydrogen peroxide).
Figure 4:
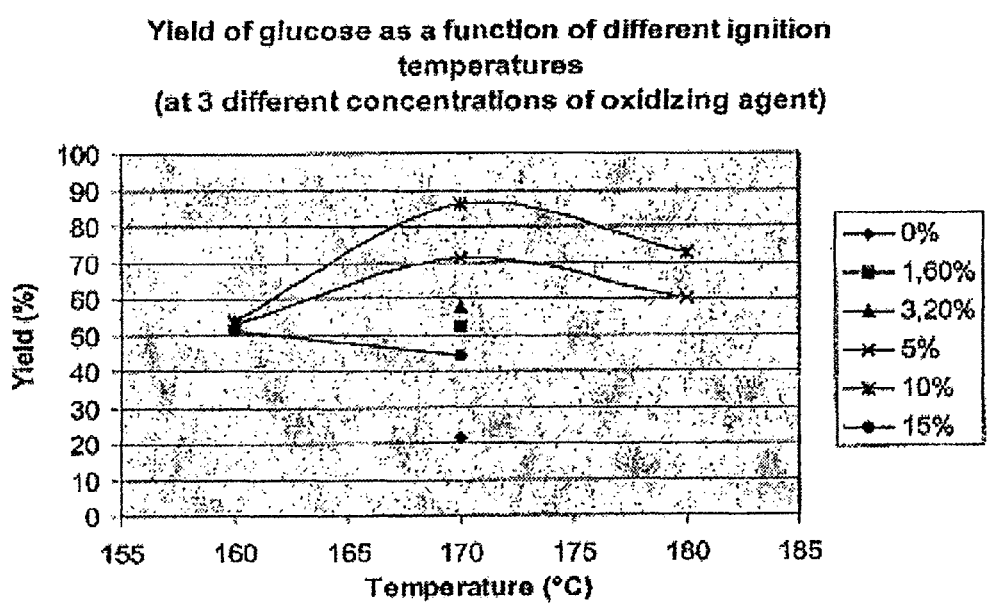
FIG. 4 is a graph showing the yield of glucose resulting from the claimed treatment of straw.
Figure 5:
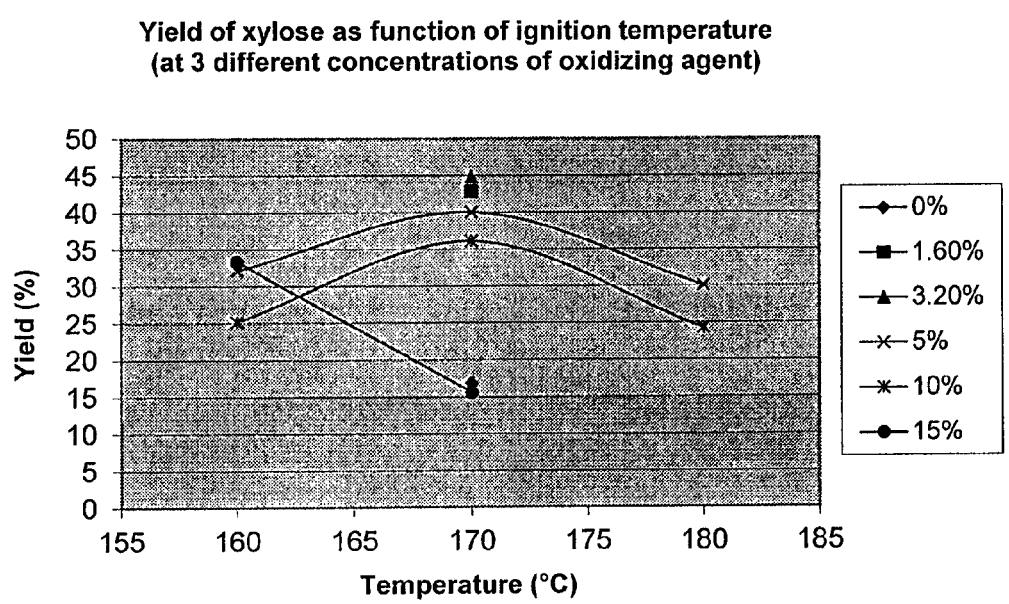
FIG. 5 is a graph showing the yield of xylose resulting from the claimed treatment of straw.

Combined Thermal Hydrolysis, Wet Oxidation (Hydrogen Peroxide) and Wet Explosion of Straw Experiments were carried out with 0%, 2%, 4%, 6%, 12% and 18% hydrogen peroxide respectively at temperatures of 170° C. The experiments were carried out so that on the day before the treatment, the weight of the biomass was weighed and water was added to the biomass. This mixture was conveyed to the reactor and heated to the desired temperature. This was maintained for approximately 10 min, whereafter the desired amount of hydrogen peroxide was added and the pressure in the process increased to 20-24 bar. After termination of the reaction (indicated by falling pressure and temperature), the pressure of the biomass was released at 15 bar to an expansion tank. After cooling to approximately 50° C. a biomass sample was taken for analysis.

The Concentration of Material

The concentration of lignocellulosic material was between 200 g straw/l water and 350 g straw/l water, preferably 250 g straw/l water or a 20% suspension.

Temperature

In order to ensure ignition of the used material (straw) the temperature was usually above 155° C., preferably between 160° C. and 180° C.

Post Treatment

After cooling the treated material was furthermore treated with enzymes (cellulases) in order to convert the carbohydrates to monohydrates before fermentation into ethanol. Furthermore, an inhibition test was carried out on the enzyme-treated media.

Results

TABLE 1

Ignition pressure and temperatures of example 1

| Measured data in the following experiments | Steam temperature (° C.) | Ignition pressure (bar) |
| --- | --- | --- |
| 5.1 | 185 | |
| 4.1 | 170 | |
| 4.2 | 172 | 14 |
| 4.3 | 174 | 13 |
| 1.1 | 160 | 13 |
| 1.2 | 174 | 14 |
| 1.3 | 184 | 14 |
| 2.1 | 160 | 13 |
| 2.2 | 170 | 13 |
| 2.3 | 180 | 14 |
| 3.1 | 160 | 13 |
| 3.2 | 174 | 14 |
| 3.2b | 172 | 13 |
| GNS | | 13.5 |
| GNS n.1 | 160.0 | 13.5 |
| GNS n.2 | 172.7 | 13.5 |
| GNS n.3 | 182.0 | 13.5 |

TABLE 2

Total yield of carbohydrates (%) resulting from the claimed treatment of straw at different temperatures and different concentrations of oxidizing agent (hydrogen peroxide)

| Concentration of oxidizing agent | Temp. 160° C. | Temp. 170° C. | Temp. 180° C. |
| --- | --- | --- | --- |
| 0% | | 20% | |
| 1.60% | | 48% | |
| 3.20% | | 52% | |
| 5% | 44% | 57% | 47% |
| 10% | 41% | 64% | 51% |
| 15% | 43% | 32% | |

TABLE 3

Total yield of carbohydrates resulting from the claimed treatment of straw (treated at 170° C.) having a dry matter content of 25% and using hydrogen peroxide as oxidizing agent

| Oxygen/COD | Yield (g/l) |
| --- | --- |
| 0% | 41.1 |
| 2% | 98.25 |
| 3% | 103.2 |

TABLE 3-continued

Total yield of carbohydrates resulting from the claimed treatment of straw (treated at 170° C.) having a dry matter content of 25% and using hydrogen peroxide as oxidizing agent

| Oxygen/COD | Yield (g/g) |
| --- | --- |
| 0% | 0.13 |
| 2% | 0.33 |
| 3% | 0.35 |

| Oxygen/COD | Total yield of carbohydrates (%) |
| --- | --- |
| 0% | 20 |
| 2% | 48 |
| 3% | 52 |

TABLE 4

Yield of glucose resulting from the claimed treatment of straw at three different temperatures and different concentrations of oxidizing agent

| Concentration of oxidizing agent (hydrogen peroxide) | Temp. 160° C. | Temp. 170° C. | Temp. 180° C. |
| --- | --- | --- | --- |
| 0% | | 22 | |
| 1.60% | | 52 | |
| 3.20% | | 57 | |
| 5% | 53 | 71 | 60 |
| 10% | 54 | 86 | 72 |
| 15% | 51 | 44 | |

TABLE 5

Yield of glucose resulting from the treatment of straw (treated at 170° C.) having a dry matter content of 25% and using hydrogen peroxide as an oxidizing agent

| Oxygen/COD | Yield (g/l) |
| --- | --- |
| 0% | 25.45 |
| 2% | 59.60 |
| 3% | 63.85 |

| Oxygen/COD | Yield (g/g) |
| --- | --- |
| 0% | 0.08 |
| 2% | 0.20 |
| 3% | 0.22 |

| Oxygen/COD | Yield (%) |
| --- | --- |
| 0% | 22 |
| 2% | 52 |
| 3% | 57 |

TABLE 6

Yield of xylose resulting from the claimed treatment of straw at three different temperatures and different concentrations of oxidizing agent

| Concentration of oxidizing agent (hydrogen peroxide) | Temp. 160° C. | Temp. 170° C. | Temp. 180° C. |
| --- | --- | --- | --- |
| 0% | | 17% | |
| 1.60% | | 43% | |
| 3.20% | | 45% | |
| 5% | 32% | 40% | 30% |
| 10% | 25% | 36% | 24% |
| 15% | 33% | 16% | |

TABLE 7

Yield of xylose resulting from the claimed treatment of straw
(treated at 170° C.) having a dry matter content of 25%
and using hydrogen peroxide as an oxidizing agent

| Oxygen/COD | Yield (g/l) |
|---|---|
| 0% | 15.65 |
| 2% | 38.65 |
| 3% | 39.35 |

| Oxygen/COD | Yield (g/g) |
|---|---|
| 0% | 0.05 |
| 2% | 0.13 |
| 3% | 0.13 |

| Oxygen/COD | Yield (%) |
|---|---|
| 0% | 17 |
| 2% | 43 |
| 3% | 45 |

The Thermal Hydrolysis, Wet Oxidation and Wet Explosion Process

In the interval 160° C.-180° C. no dependence between temperature and TCOD (Total COD), OCOD (dissolved materials COD) in the treated material, was observed.

Inorganic material is apparently not decomposed by the treatment, it is thus possible to use this as a basis of reference.

TCOD/g of dry matter in the treated material were in all batches measured to 1.3.

In the wet explosion approximately 25% of the incoming amount of water is evaporated.

In the temperature interval 160° C.-180° C. the sum of steam- and oxygen-pressure was maintained between 13.5 and 14.0 bar in order to oxidize the material. The steam-pressure before addition of hydrogen peroxide was fixed solely based on the temperature, so to understand that at least such an amount of hydrogen peroxide was added that would cause the total pressure at the liberation of oxygen to exceed 13.5 to 14.0 bar.

Total COD out of the reactor constitute between 60 and 95% of the incoming amount. When oxidation amounts compared to incoming COD exceeds 10% a stabil TCOD of approximately 60%, OCOD of approximately 25% and a UCOD of approximately 35% are observed. At an oxidation amount smaller than 10% a distinctive dependency is observed. The lost amount of COD is partly due to the oxidation (small amounts) and partly to the formation of acetic acid that evaporates in the wet explosion. The greatest loss occurs in connection with the evaporation of acetic acid, because the pH-value is approximately 2 and the steam pressure of acetic acid is 1 bar at 117° C. In a commercial plant the acetic acid could be gathered and utilized in e.g. biogas production.

If the addition of oxidizing agent is 0%, TCOD constitutes 95%, OCOD 13% and UCOD 82% of the incoming amount. The 5% loss is mainly constituted of acetic acid evaporating in the flashing process, cf. above.

Liberation of Carbohydrates

Generally, the largest yields for both glucose and xylose are obtained at a temperature of approximately 170° C. The yields at 160 and 180° C. were smaller than at 170° C. A few measurements showed yields of glucose and xylose above 90%, with a content of carbohydrate in straw of 0.32 g glucose/g and 0.12 g xylose/g respectively.

Oxidizing Agent

The optimal yield is obtained in the interval 5 to 10% (oxidation amount compared to COD amount). However, it was possible to treat suspensions of up to 35% in water.

Combined Thermal Hydrolysis, Wet Oxidation and Wet Explosion of Straw Pellets

In the following examples 2-6 the estimation of glucose, xylose and ethanol yields from straw pellets were based on the information that 1 g straw pellet (dry matter) contains 0.36 g glucose and 0.22 g xylose respectively (according to the index list of the straw pellets produced by E2 in Køge, Denmark). The calculation of the ethanol yield is based on a theoretical yield from glucose fermentation of 0.50 g ethanol/g glucose and a theoretical yield from xylose fermentation of 0.40 g ethanol/g xylose. More specifically the calculations of the glucose, xylose and ethanol yields from straw pellets, both with and without prior acidic treatment, were based on the below formulas.

Calculations of glucose, xylose and ethanol yields from straw pellets without acid treatment:

$$\frac{L_{ethanol}}{t_{TS}} = \frac{G \cdot Y_{enz} \cdot Y_{ferm} + X \cdot Y_{enz} \cdot Y_{ferm}}{\rho_{ethanol}}$$

$$\frac{L_{ethanol}}{t_{TS}}$$

L ethanol per ton dry matter (TS) after wet oxidation
G Glucose content of straw pellets of 0.36 g glucose pr g dry matter
X Xylose content of straw pellets of 0.22 g xylose pr g dry matter
$Y_{enz}$ Total yield of the pre-treatment and the enzymatic hydrolysis
$Y_{ferm}$ Yield of the fermentation of 0.50 g ethanol/g glucose and 0.40 g ethanol/g xylose
$\rho_{ethanol}$ The density of ethanol of 0.789 g/ml Calculations of glucose, xylose and ethanol yields from straw pellets with acidic treatment:

$$\frac{L_{ethanol}}{t_{TS}} = \frac{G \cdot Y_{enz} \cdot Y_{ferm} + X \cdot Y_{enz} \cdot Y_{ferm} + X \cdot Y_{acid} \cdot Y_{ferm}}{\rho_{ethanol}}$$

$$\frac{L_{ethanol}}{t_{TS}}$$

L ethanol per ton dry matter (TS) after wet oxidation
G Glucose content of straw pellets of 0.36 g glucose pr g dry matter
X Xylose content of straw pellets of 0.22 g xylose pr g dry matter
$Y_{enz}$ Total yield of the pre-treatment and the enzymatic hydrolysis
$Y_{ferm}$ Yield of the fermentation 0.50 g ethanol/g glucose and 0.40 g ethanol/g xylose
$Y_{acid}$ The 75% xylose elimination by the acid treatment
$\rho_{ethanol}$ The density of ethanol of 0.789 g/ml Furthermore, in order to reach the maximal yield of glucose, xylose and ethanol the enzymatic hydrolysis in the following examples is performed with high enzyme loads and long hydrolysis times utilizing a simple shaking device without a pH controlling device. Further optimization of the enzymatic hydrolysis, and thus the final yields of glucose, xylose and ethanol, might be achieved by using orbital-, rotary or similar shaking devices performing optimal agitation and having concurrent pH registration in order to establish a pH in the substrate according to the pH optima of the enzymes. In all of the following examples the yields of glucose and xylose respectively were measured after enzymatic hydrolysis utilizing the commercially available cellulases, Celluclast® and Novozymes®188.

The subsequent experiments were carried out in batch facilities, wherein the increase of the pressure was limited by safety valves, set to a maximum of 25 bar. Accordingly, in the following examples (except Example 3) the overall decompression during the wet explosion was approximately 20-25 bar, i.e. from approximately 25 bar to approximately 0 bar.

EXAMPLE 2

Effect of Temperature

In order to evaluate the effect of the temperature in relation to the glucose, xylose and ethanol yields, experiments were conducted with straw pellets utilizing 25 bar of atmospheric air as the oxidizing agent. The temperature was measured in the bottom of the reactor after the addition of the oxidizing agent.

TABLE 8

| Temperature | 170° C. | 180° C. |
|---|---|---|
| Material | straw pellets | straw pellets |
| Oxidazing agent | 25 bar atmospheric air | 25 bar atmospheric air |
| Yield of glucose | 57% | 87-90% |
| Yield of xylose | 67% | 85-94% |
| L ethanol per ton dry matter after wet oxidation | 205 | 293-310 |

Using straw pellets (compared to straw used in example 1) as lignocellulosic material a 10° C. increase of temperature, from 170° C. to 180° C., resulted in significantly improved yields of glucose, xylose as well as ethanol. Accordingly, the composition of the lignocellulosic material, i.a. the dry matter concentration, the fiber sizes, the ratios of lignin, cellulose and hemicellulose, as well as the oxidizing agent used, effected the temperature optima in the claimed process.

EXAMPLE 3

Effect of Wet Explosion (Flashing)

In order to establish the effect of the wet explosion, straw pellets were subjected to thermic hydrolysis, wet oxidization and wet explosion. The net drop of pressure in the wet explosion was 20 bar and 0 bar respectively, i.e. a drop of pressure from 20 bar to 0 bar and from 0 bar to 0 bar respectively. Nitrogen and atmospheric air was used as a "control agent" and an oxidizing agent respectively. All batches were carried out at temperature of 180° C. and the pressures of 0 bar were obtained by cooling down the reactor and subsequently slowly neutralizing the pressure.

TABLE 9

| Wet explosion pressure | 0 bar | 20 bar | 0 bar | 20 bar |
|---|---|---|---|---|
| Material | straw pellets | straw pellets | straw pellets | straw pellets |
| Oxidizing agent or "control agent" | Nitrogen | Nitrogen | 25 bar atm. air | 25 bar atm. air |
| Yield of glucose | 65% | 63% | 83% | 87-90% |
| Yield of xylose | 75% | 73% | 89% | 85-94% |
| L ethanol per ton dry matter after wet oxidation | 232 | 225 | 289 | 293-310 |

The drop of pressure of the wet explosion step in the treatment of straw pellets did not have any effects on the final glucose, xylose or ethanol yields when nitrogen was used. When 25 bar of atmospheric air was used as oxidizing agent there was a small but still significant increase by introducing the wet explosion step. This effect can be expected to increase with a reactor design having an upper limit above 25 bar.

EXAMPLE 4

Effect of Oxidizing Agent and Acidic Treatment

This experiment, the purpose of which was to establish the importance of the oxidizing agent as well as the effect of an optional use of an acidic treatment (e.g. acidic prehydrolysis) in relation to the yields of glycose, xylose and ethanol from straw pellets, was carried out with atmospheric air and hydrogen peroxide as oxidizing agents and nitrogen as a "control agent". In the acidic treatment straw pellets having a 10% dry matter content was treated with 0.7% $H_2SO_4$ in 130° C. for 1 hour.

TABLE 10

| Material | Straw pellets pretreatet with acid | Straw pellets pretreatet with acid | Straw pellets | Straw pellets | Straw pellets pretreatet with acid | Straw pellets |
|---|---|---|---|---|---|---|
| Oxidizing agent and "control agent" | 0 bar atm. air | 25 bar atm. air | 10 bar nitrogen | 5% $H_2O_2$ | 3.3% $H_2O_2$ | 25 bar atm. air |
| Yield of glucose | 95-100% | 97% | 63% | 100-104% | 98% | 87-90% |

A significant positive effect is seen on glucose, xylose and ethanol yields with the addition of an oxidizing agent (air as well as hydrogen peroxide) when compared to the "control agent" nitrogen, when using straw pellets as substrate. Using hydrogen peroxide is advantageous compared to air when looking at the glucose yield. As is further observed from the experiment the yield of glucose is significantly improved subsequent to acidic treatment of straw pellets using 25 bar atmospheric air as the oxidizing agent.

EXAMPLE 5

Effect of Straw Versus Straw Pellets

A direct comparison was performed of two lignocellulosic biomasses in order establish a possible influence of i.a. particle/fiber sizes and dry matter concentration i relation to the final yields of glucose, xylose and ethanol.

TABLE 11

| Temperature | 180° C. | 180° C. |
|---|---|---|
| Material | Straw | Straw pellets |
| Oxidizing agent | 25 bar atm. air | 25 bar atm. Air |
| Yield of glucose | 89% | 87-90% |
| Yield of xylose | 93% | 85-94% |
| L ethanol per ton dry matter after wet oxidation | 307 | 293-310 |

By using straw and straw pellets as the lignocellulosic materials in the process according to the present invention no significant differences was observed in relation to the yields of glucose, xylose and ethanol respectively, suggesting that the process favorably also can be applied on biomasses having larger fiber sizes than e.g. straw pellets.

EXAMPLE 6

Effect of Dry Matter Concentration

In order to establish possible differences in the yields of xylose, glucose and ethanol obtained from straw pellets having different dry matter concentrations, experiments utilizing hydrogen peroxide and air as oxidizing agents were carried out. The dry matter concentrations of straw pellets and straw pellets treated with acid were measured after the wet oxidation.

TABLE 12

| | Dry matter concentration (%) | | | | |
|---|---|---|---|---|---|
| | 4 | 21.5 | 26.8 | 11.4 | 17.6 |
| Material | Straw pellets | Straw pellets | Straw pellets pretreatet with acid | Straw pellets | Straw pellets |
| Oxidizing agent | 5% $H_2O_2$ | 5% $H_2O_2$ | 10 bar atm. air | 25 bar atm. air | 25 bar atm. air |
| Yield of glucose | 89% | 95% | 95% | 90% | 87% |
| Yield of xylose | 70% | 74% | 24% | 94% | 85% |
| L ethanol per ton dry matter after wet oxidation | 281 | 299 | 327 | 310 | 293 |

By increasing the dry matter concentrations as indicated in table 12, a significant reduction of the glucose, xylose and ethanol yields are observed, regardless of the oxidizing agent used. However, the reduced yields (although significant) are relatively modest and is probably a result of inadequate agitation rather than a result of the increased dry matter concentration.

REFERENCES

Bjerre, A. B., Olesen, A. B., Fernqvist, T., Plöger, A., and Schmidt, A. S. (1996) Pretreatment of wheat straw using combined wet oxidation and alkaline hydrolysis resulting in convertible cellulose and hemicellulose. Biotechnol. Bioeng. 49(5), 568-577.

Holtzapple, M. T., Jun, J. H., Ashok, G., Patibandla, S. L., and Dale, B. E. (1991) The Ammonia Freeze Explosion (AFEX) Process-A Practical Lignocellulose Pretreatment. Appl. Biochem. Biotech. 28-9, 59-74.

Klinke, H. B., Ahring, B. K., Schmidt, A. S., and Thomsen, A. B. (2002) Characterization of degradation products from alkaline wet oxidation of wheat straw. Bioresour. Technol. 82(1), 15-26.

Martin, C., Galbe, M., Nilvebrant, N. O., and Jonsson, L. J. (2002) Comparison of the fermentability of enzymatic hydrolyzates of sugarcane bagasse pretreated by steam explosion using different impregnating agents. Appl. Biochem. Biotech. 98 699-716.

Morjanoff, P. J. and Gray, P. P. (1987) Optimization of steam explosion as a method for increasing susceptibility of sugarcane bagasse to enzymatic saccharification. Biotechnol. Bioeng. 29(6), 733-741.

Palmqvist, E. and Hahn-Hägerdal, B. (2000) Fermentation of lignocellulosic hydrolysates. II: inhibitors and mechanisms of inhibition. Bioresour. Technol. 74(1), 25-33.

Van Walsum, G. P., Allen, S. G., Spencer, M. J., Laser, M. S., Antal, M. J., and Lynd, L. R. (1996) Conversion of lignocellulosics pretreated with liquid hot water to ethanol. Appl. Biochem. Biotech. 57-8 157-170.

The invention claimed is:

1. Method for treatment of a material consisting of biomass or organic waste containing lignocellulosic material, wherein said material has particle/fiber sizes between 4 and 50 cm and:
   is subjected to thermal hydrolysis at a temperature above 140° C. maintained for 5-30 minutes followed by
   oxidation at a pressure of 15-35 bar and a temperature of 170-210° C. maintained for 1-30 minutes followed by
   wet explosion carried out by means of reducing the pressure from 5-35 bar to atmospheric pressure,
with the aim of rendering carbohydrates of the material more available for a subsequent reaction by enzymatic hydrolysis and/or fermentation.

2. Method according to claim 1, wherein the method is carried out as a batch process.

3. Method according to claim 1 or 2, wherein the material contains more than 5% (w/w) lignin.

4. Method according to claim 1, wherein the material has a dry matter content between 10 and 50%.

5. Method according to claim 1, wherein the material is chosen from the group consisting of straw, wood, fibres, baits, paper pulp, slurry and household waste.

6. Method according to claim 1, wherein the material has particle/fiber sizes between 5 and 20 cm.

7. Method according to claim 6, wherein the material has particle sizes in the range of 5-20 cm.

8. Method according to claim 1, wherein the lignocellulosic material is treated with acid as a pre-treatment step.

9. Method according to claim 1, wherein the thermal hydrolysis is carried out by means of heating to 140-200° C. at saturation pressure, and where said conditions are maintained for 5-30 minutes.

10. Method according to claim 9, wherein the thermal hydrolysis is carried out by means of heating to 160-180° C.

11. Method according to claim 9, wherein said conditions are maintained for 10-20 minutes.

12. Method according to claim 1, wherein the oxidation is carried out by means of adding oxygen, hydrogen peroxide and/or air in an amount corresponding to 2-20% of the chemical oxygen demand content of said material, heating to 180-200° C., and maintaining these conditions for 5-25 minutes, wherein the pressure of the biomass after termination of the oxidation reaction optionally is released to 5-10 bar.

13. Method according to claim 12, wherein the conditions are maintained for 10-20 minutes.

* * * * *